US00PP35610P2

(12) United States Plant Patent
Wansinck

(10) Patent No.: US PP35,610 P2
(45) Date of Patent: Jan. 30, 2024

(54) ILEX PLANT NAMED 'JENNY'

(50) Latin Name: *Ilex crenata*
Varietal Denomination: Jenny

(71) Applicants: Stef Wansinck dienstverlening, Hazerswoude-Dorp (NL); Niels Wansinck dienstverlening, Hazerswoude-Dorp (NL)

(72) Inventor: Barry Wansinck, Hazerswoude-Dorp (NL)

(73) Assignees: Stef Wansinck Dienstverlening, Hazerswoude-Dorp (NL), PART INTEREST; Niels Wansinck Dienstverlening, Hazerswoude-Dorp (NL), PART INTEREST ( * ) Notice: Subject to any disclaimer, the term of this patent is extended or adjusted under 35 U.S.C. 154(b) by 0 days.

(21) Appl. No.: 18/201,226

(22) Filed: May 24, 2023

(51) Int. Cl.
*A01H 5/12* (2018.01)
*A01H 6/00* (2018.01)

(52) U.S. Cl.
USPC ..... Plt./247

(58) Field of Classification Search
USPC ..... Plt./247
CPC ..... A01H 5/12; A01H 5/00; A01H 6/00
See application file for complete search history.

(56) References Cited

U.S. PATENT DOCUMENTS

PP29,992 P2 * 12/2018 van Nijnatten ..... A01H 6/00
Plt./247

* cited by examiner

*Primary Examiner* — June Hwu
(74) *Attorney, Agent, or Firm* — Penny J. Aguirre

(57) ABSTRACT

A new cultivar of *Ilex crenata* plant named 'Jenny' that is characterized by its highly vigorous growth habit with strong and fast-growing root systems, its flat leaves, its foliage that is bright green in color when young and dark green in color when mature, its male flowers that lack fruit production, and its neat and densely branched plant habit.

2 Drawing Sheets

Botanical classification: *Ilex crenata.*
Variety denomination: 'Jenny'.

CROSS REFERENCE TO A RELATED APPLICATION

This application is related to a European plant breeders' rights application filed on Oct. 16, 2020, application No. 2020/2556. The Applicant received the information for the Plant breeders' rights application directly from the Inventor.

BACKGROUND OF THE INVENTION

The present invention relates to a new and distinct cultivar of *Ilex crenata* and will be referred to hereafter by its cultivar name, 'Jenny'. 'Jenny' is a new cultivar of Japanese holly grown for use as an ornamental landscape plant.

'Jenny' was discovered by the Inventor as a chance seedling in a trial field in Hazerswoude-Dorp, The Netherlands in 2013. The parentage is unknown as there were numerous cultivars of *Ilex crenata* growing in the trial field.

Asexual propagation of the new cultivar was first accomplished by the Inventor using softwood stem cuttings in 2013 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Jenny' as a unique cultivar of *Ilex.*

1. 'Jenny' exhibits a highly vigorous growth habit with strong and fast-growing root systems.
2. 'Jenny' exhibits flat leaves.
3. 'Jenny' exhibits foliage that is bright green in color when young and dark green n color when mature.
4. 'Jenny' exhibits male flowers only and lacks fruit production.
5. 'Jenny' exhibits a neat and densely branched plant habit.

'Jenny' can be most closely compared to the *Ilex crenata* cultivars 'Caroline Upright' (not patented), 'Glory Gem' (not patented) and 'Convexa' (not patented). 'Caroline Upright' differs from 'Jenny' in having weaker and slower growing root system, young shoots that are darker green in color, a slower growing plant habit, leaves that are larger in size and a less dense branching habit. 'Glory Gem' differs from 'Jenny' in having thicker leaves that are less flat and smaller in size, young foliage that is darker green in color, a slower growing root system, and has a higher susceptibility to disease. 'Convexa' differs from 'Jenny' in having leaves that are less flat, foliage that is darker green in color, a higher susceptibility to disease, a less compact and more irregular growth habit, and in being a female plant that produces berries.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by vida-verde, Arboretum, Lucan Garden Centre, Proctors Nursery, bijstox, Hornbach, Clarenbridge Garden Centre, floraxchange, pelckmans, Stewarts Garden Centres, and Ebay.

BRIEF DESCRIPTION OF THE DRAWINGS

The accompanying color photographs illustrate the overall appearance and distinct characteristics of six-month-old plants of the new cultivar as grown outdoors in a 17-cm containers in Muge, Portugal.

The photograph in FIG. 1 provides a side view of the plant habit of 'Jenny'.

Figure 1:
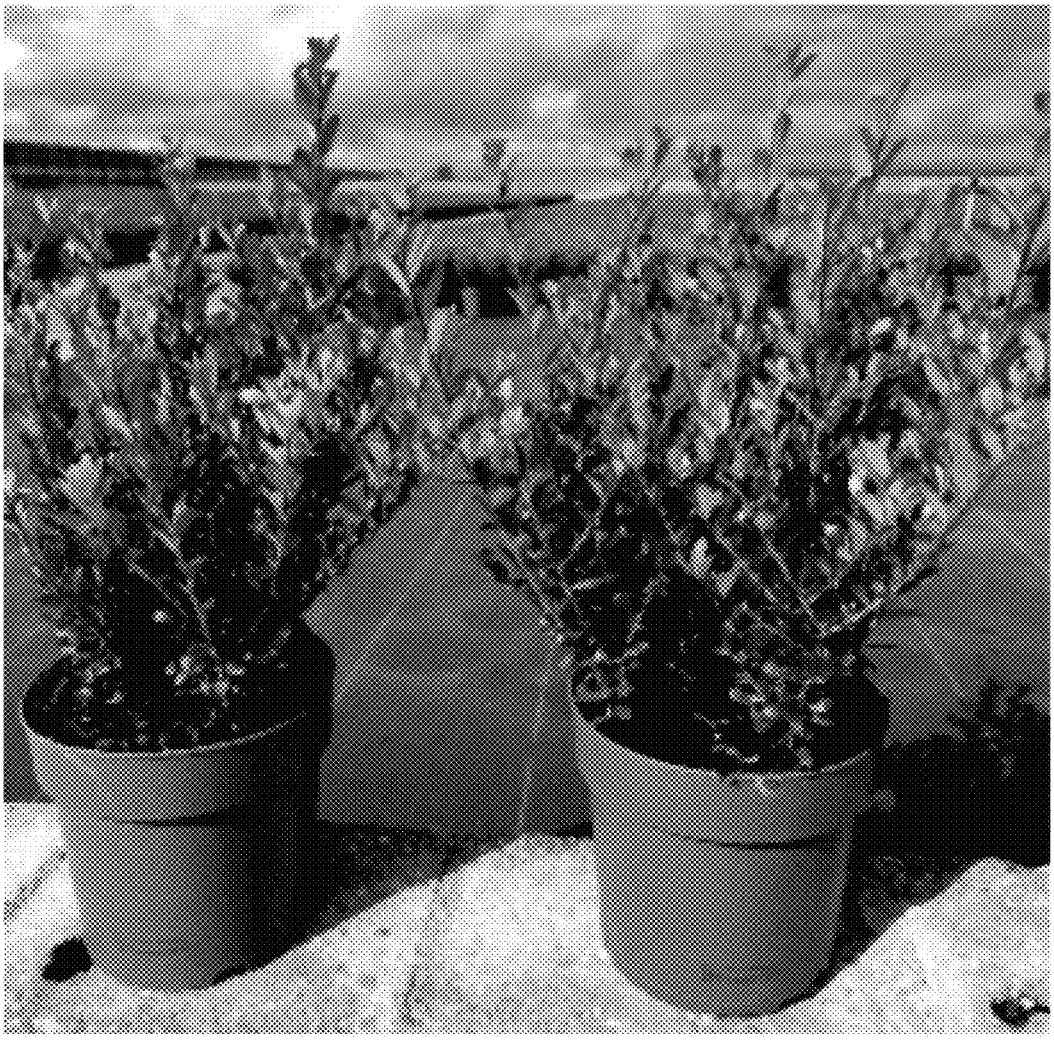
Figure 2:
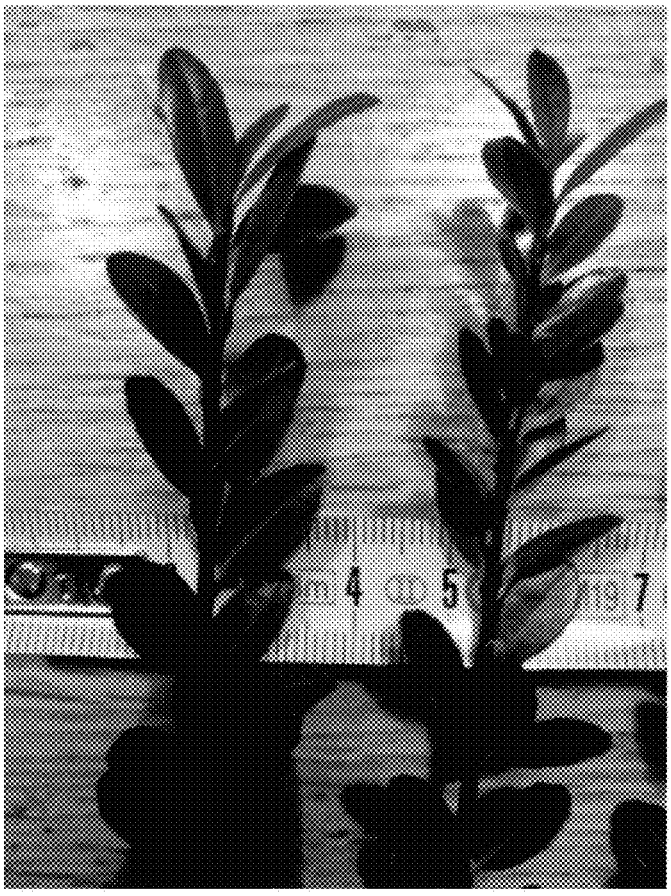

The photograph in FIG. 2 provides a close-up view of the mature foliage of 'Jenny'.

Figure 3:
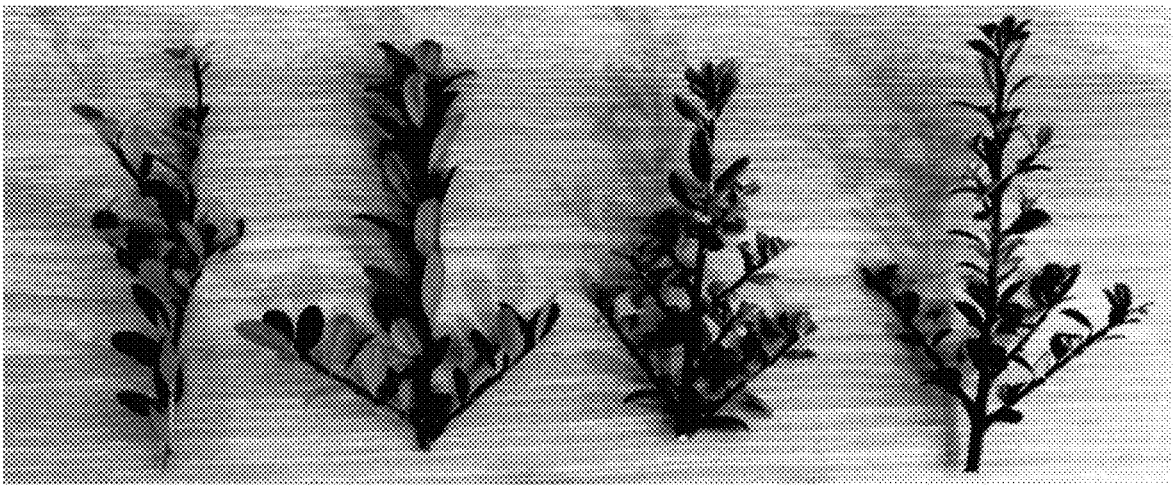

The photograph in FIG. 3 provides a comparison of the foliage between 'Jenny' (left) and towards the right 'Carolina Upright', 'Convexa', and 'Glory Gem'.

The colors in the photographs may differ slightly from the color values cited in the detailed botanical description, which accurately describe the colors of the new *Ilex*.

DETAILED BOTANICAL DESCRIPTION

The following is a detailed description of one-year-old plants of the new cultivar grown outdoors in 19-cm containers in Hazerswoude-Dorp, The Netherlands. The phenotype of the new cultivar may vary with variations in environmental, climatic, and cultural conditions, as it has not been tested under all possible environmental conditions.

The color determination is in accordance with The 2015 Colour Chart of The Royal Horticultural Society, London, England, except where general color terms of ordinary dictionary significance are used.

General description:

*Blooming period*.—May into June in The Netherlands.
*Plant type*.—Evergreen, perennial shrub.
*Plant habit*.—Compact, semi-upright.
*Height and spread*.—Reaches an average of 30 cm in height and width as a one-year-old plant in a 19-cm container, reaches an average of 80 cm in height and 45 cm in width when grown in the landscape without pruning.
*Cold hardiness*.—At least to U.S.D.A Zone 7a.
*Diseases and pests*.—No susceptibility to diseases or pests has been observed.
*Root description*.—Densely fibrous and 165C in color.
*Propagation*.—Softwood stem cuttings.
*Root development*.—An average of 4 weeks for root initiation and 12 months to produce a rooted plant in a 19-cm container in Portugal.
*Growth rate*.—High, an average of 10 weeks earlier than is typical of the species.

Branch description:

*Branching*.—Densely branching; 3 main branches each with an average of 21 lateral branches.
*Stem size*.—Main stems; 2.7 cm in length, 8 mm in diameter, lateral branches; 4 mm in diameter, 18 cm in length.
*Stem surface*.—Slightly glossy, older stems covered with smooth bark.
*Stem shape*.—Rounded.
*Stem aspect*.—An average of 55° (90° is vertical).
*Stem strength*.—Strong.
*Stem color*.—Young stems; N77A, mature stems; 146B, older stems; 199C.
*Internode length*.—Average of 5 mm.

Foliage description:

*Leaf shape*.—Elliptic.
*Leaf division*.—Simple.
*Leaf base*.—Acute.
*Leaf apex*.—Obtuse.
*Leaf venation*.—Pinnate, both surfaces 144B.
*Leaf margins*.—Entire.
*Leaf arrangement*.—Alternate.
*Leaf aspect*.—Flat.
*Leaf attachment*.—Petiolate.
*Leaf surface*.—Both surfaces glossy and smooth.
*Leaf size*.—Average of 2.2 cm in length and 1 cm in width.
*Leaf quantity*.—Average of 50 per lateral branch.
*Leaf color*.—Young leaves upper surface 144B, young leaves lower surface 144C, mature upper surface 137A, mature lower surface 146C.
*Petioles*.—Average of 4 mm in length and 1 mm in diameter, strong, smooth and glabrous surface, color; upper surface 144B with 199A, lower surface 199A, base 77A.

Flower description:

*Inflorescence type*.—Cymes of campanulate-shaped flowers on axillary nodes of lateral branches.
*Lastingness of inflorescence*.—About 2 weeks, self-cleaning.
*Inflorescence size*.—An average of 7 mm in height and diameter.
*Flower fragrance*.—None.
*Flower number*.—3 to 4 per inflorescence.
*Flower aspect*.—Rotate, cup-shaped.
*Flower bud*.—Round-oblong in shape, an average of 1 mm in length and width, color; a blend of N155A and 144C, base 144D.
*Flower form*.—Campanulate.
*Flower size*.—An average of 4 mm in width and 1 mm in depth.
*Petal*.—An average of 4, rotate, ovate in shape, an average of 2 mm in length, 3 mm in width, obtuse apex, rounded base, entire margin, color upper and lower surface N155A, smooth and glabrous on upper and lower surfaces.
*Sepals*.—An average of 4, ovate in shape, an average of 0.7 mm in length and width, broadly acute apex, fused based, entire margin, color upper and lower surfaces 144C, smooth and glabrous on upper and lower surfaces.
*Peduncles*.—Oval in shape, an average of 3 mm in length and 0.5 mm in width, moderately strong, 144C in color, smooth and glabrous surface.
*Pedicels*.—Oval in shape, an average of 4 mm in length and 0.3 mm in width, moderately strong, 144C in color, smooth and glabrous surface.

Reproductive organs:

*Gynoecium*.—Not present, male flowers only.
*Androecium*.—4 stamens, anthers; oblong in shape, 3 mm in length, 0.2 mm in width, 1D in color, filaments; an average of 1 mm in length and 1D in color, pollen is moderate and 1A in color.
*Seed and fruit*.—Not produced as only male flowers are present.

It is claimed:

1. A new and distinct cultivar of *Ilex* plant named 'Jenny' as herein illustrated and described.

* * * * *